(12) United States Patent
Lv et al.

(10) Patent No.: US 9,187,394 B2
(45) Date of Patent: Nov. 17, 2015

(54) METHOD FOR SYNTHESIZING 2,7-DIMETHYL-2,4,6-OCTATRIENE-1,8-DIALDEHYDE

(71) Applicants: NANJING UNIVERSITY OF TECHNOLOGY, Nanjing (CN); Zhejiang Medicine Co., Ltd. Xinchang Pharmaceutical Factory, Donglu (CN)

(72) Inventors: Chunlei Lv, Huancheng Donglu (CN); Shiqing Pi, Huancheng Donglu (CN); Jianhui Chen, Huancheng Donglu (CN); Dingqiang Lu, Huancheng Donglu (CN); Pingkai Ouyang, Huancheng Donglu (CN)

(73) Assignees: Nanjing University of Technology, Nanjing (CN); Zhejiang Medicine Co., Ltd. Xinchang Pharmaceutical Factory, Donglu (CN)

( * ) Notice: Subject to any disclaimer, the term of this patent is extended or adjusted under 35 U.S.C. 154(b) by 0 days.

(21) Appl. No.: 14/369,164

(22) PCT Filed: Dec. 10, 2012

(86) PCT No.: PCT/CN2012/001666
§ 371 (c)(1),
(2) Date: Jun. 26, 2014

(87) PCT Pub. No.: WO2013/097284
PCT Pub. Date: Jul. 4, 2013

(65) Prior Publication Data
US 2014/0378711 A1  Dec. 25, 2014

(30) Foreign Application Priority Data
Dec. 26, 2011  (CN) .......................... 2011 1 0440215

(51) Int. Cl.
C07C 45/42 (2006.01)
C07C 45/52 (2006.01)
C07C 1/32 (2006.01)
C07C 41/06 (2006.01)
C07C 41/18 (2006.01)
C07C 41/22 (2006.01)
C07F 9/38 (2006.01)

(52) U.S. Cl.
CPC ................. *C07C 45/42* (2013.01); *C07C 1/324* (2013.01); *C07C 41/06* (2013.01); *C07C 41/18* (2013.01); *C07C 41/22* (2013.01); *C07C 45/52* (2013.01); *C07F 9/38* (2013.01)

(58) Field of Classification Search
CPC ........ C07C 45/42; C07C 41/06; C07C 41/18; C07C 41/22; C07C 1/324; C07F 9/38
USPC .......................................................... 568/491
See application file for complete search history.

(56) References Cited

U.S. PATENT DOCUMENTS

| | | | | |
|---|---|---|---|---|
| 5,276,209 A * | 1/1994 | Jaedicke et al. | ............... | 560/260 |
| 5,471,005 A * | 11/1995 | Babler | ............... | 568/459 |
| 6,153,769 A * | 11/2000 | Ruttimann | ............... | 549/430 |
| 6,297,416 B1 * | 10/2001 | Koo et al. | ............... | 585/351 |
| 6,326,519 B1 * | 12/2001 | Koo et al. | ............... | 568/60 |
| 6,403,838 B1 * | 6/2002 | Koo et al. | ............... | 568/459 |

\* cited by examiner

*Primary Examiner* — Sikarl Witherspoon
(74) *Attorney, Agent, or Firm* — William D. Hare, Esq.; McNeely, Hare & War, LLP

(57) ABSTRACT

Provided in the present invention is a method for synthesizing 2,7-dimethyl-2,4,6-octatriene-1,8-dialdehyde. The synthesis method comprises the following steps: (1) adding acetaldehyde diethyl acetal and ethyl-(1-propenyl)-ether under the effect of a catalyst to produce 1,1,3-triethoxy-2-methyl-butane; (2) pyrolysis synthesizing 1,1,3-triethoxy-2-methyl-butane under the catalytic effects of isoquinoline and p-Toluenesulfonic acid to produce 1-methoxy-2-methyl-1,3-butadiene; (3) dissolving 1-methoxy-2-methyl-1,3-butadiene in anhydrous ethanol solvent for synthesis with a phase transfer catalyst, cetyl-trimethyl ammonium bromide, and a chlorinating agent, trichloroisocyanuric acid, to generate 4,4-diethoxy-3-methyl-1-chloro-butene; (4) combining 4,4-diethoxy-3-methyl-1-chloro-butene with a triphenylphosphine salt to produce a phosphonium salt; and (5) condensing the phosphonium salt under the effects of hydrogen peroxide in conjunction with sodium carbonate solution to generate 1,1,8,8-tetramethyl-2,7-dimethyl-2,4,6-octatriene; then hydrolyzing under acidic conditions to synthesize 2,7-dimethyl-2,4,6-octatriene-1,8-dialdehyde. The present invention has a simple process route, is easy to operate, and has mild conditions, great yield, and great industrial value.

4 Claims, No Drawings

METHOD FOR SYNTHESIZING 2,7-DIMETHYL-2,4,6-OCTATRIENE-1,8-DIALDEHYDE

CROSS-REFERENCE TO RELATED APPLICATIONS

This application is a national phase application of PCT/CN2012/001666, filed on Dec. 10, 2012, which claims priority to Chinese Application No. 201110440215.1 filed on Dec. 26, 2011.

FIELD OF THE INVENTION

The present invention relates to a method for synthesizing 2,7-dimethyl-2,4,6-octatriene-1,8-dialdehyde.

BACKGROUND OF THE INVENTION 2,7-dimethyl-2,4,6-octatriene-1,8-dialdehyde (abbreviation: C-10 dialdehyde), is basically a light-yellow powder solid with a melting point of 157.0~159.0° C., and freely soluble in methanol and dichloromethane, and soluble in petroleum ether and ethyl acetate, and slightly soluble in water. C-10 dialdehyde has no special smell, and is stable at room temperature, and easily changes with a mixture of oxidant, and usually kept isolated from air. C-10 dialdehyde is a key intermediate to synthesize carotenoids compounds such as β-carotene, canthaxanthin and astaxanthin, lycopene, etc. Studies on processes of synthesizing C-10 dialdehyde is more important with widespread applications of carotenoids.

Several synthetic methods reported in the prior documents are shown as follows. Route 1: furan as a raw material reacts with methanol to produce 1,1,4,4-tetramethoxy-2-butene via two steps of addition reaction, condense the diacetal compound with propenyl ether catalyzed with Lewis acid to prepare a C10 skeleton, and then eliminate methanol and form double bond to produce the product through a treatment with base. The key technology of this route is that bromine has higher cost and large toxicity, and the chemical property is active and unstable, the side reaction with acetal is more in addition reaction, for example, the addition product still has diacetal structure. It can occur telomerization to form polymer further through condensing with propenyl ether. So controlling and separating technology of this reaction step is a key for the whole route. The particular reaction scheme is shown as Reaction Equation 1 (synthetic route 1 of C-10 dialdehyde).

Route 2: 1-ethoxy-1-propene as a raw material is added with triethyl orthoformate catalyzed with Lewis acid to prepare 1,1,3,3-tetraethoxy-2-methylpropane, and then eliminate one molecule of ethanol to form 2-methyl-3-ethoxyl-2-crotonaldehyde compound under effects of acid, and undergo an addition reaction with acetylene di-Grignard reagent, and then dehydrate to form ethylenic bond, triple bond hydrogenating to form double bond, and deprotect finally. There are seven steps to synthesize C-10 dialdehyde, and so the reaction steps are long in this process, the reaction control on the first three steps is mainly more difficult. The total yield of C-10 dialdehyde is only 21%. The particular reaction scheme is shown as Reaction Equation 2 (synthetic route 2 of C-10 dialdehyde).

Reaction Equation 1

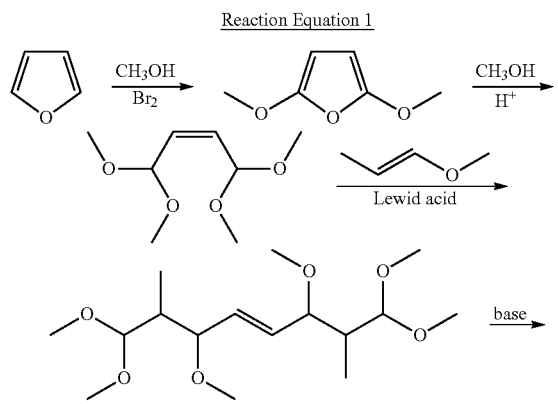

Reaction Equation 2

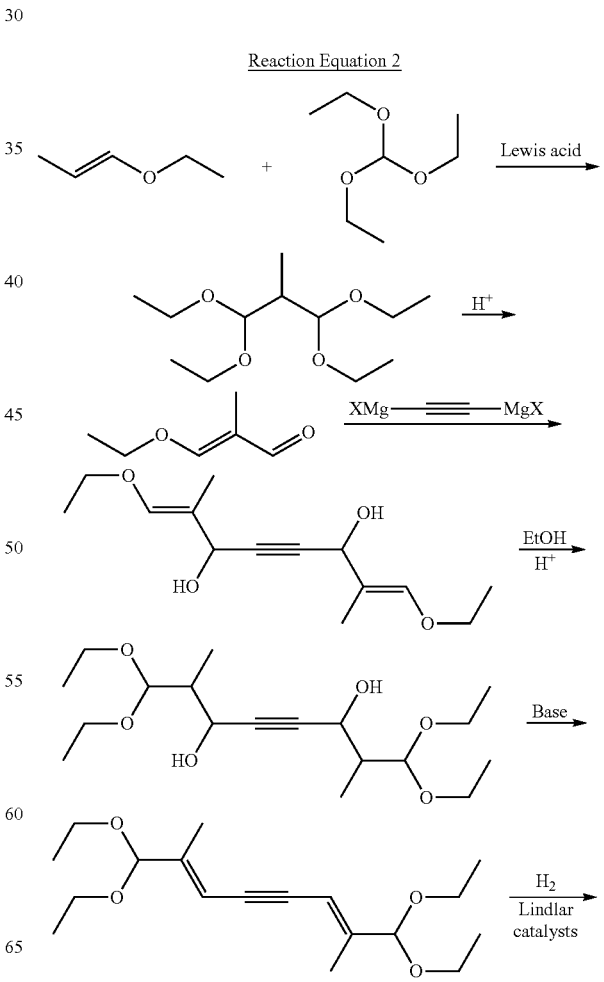

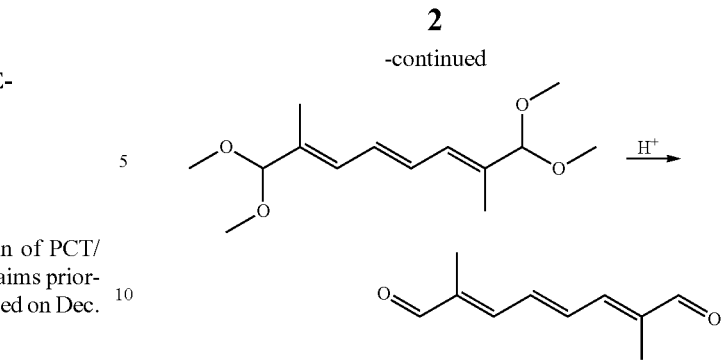

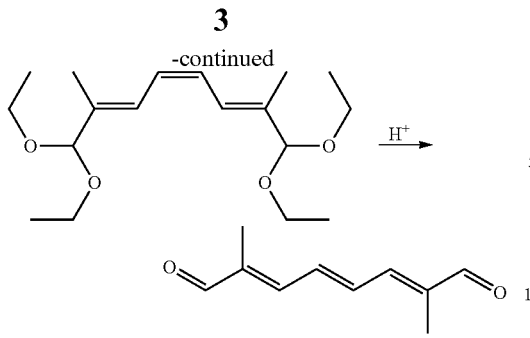

Route 3: 4-acetoxy-2-methyl-2-butene-1-aldehyde (abbreviation: C5 aldehyde) as a raw material for synthesis of vitamin A and neopentyl glycol is formed a acetal protector, and then hydrolyzed with base to produce a hydroxy compound, and halogenate the hydroxy compound, and react with sodium sulphide to form a thioether compound, and convert the thioether compound to sulfoxide via oxidation, and then react with sodium dithionite to produce the product through desulfuration, dimerization and condensation. The particular reaction scheme is shown as Reaction Equation 3 (synthetic route 3 of C-10 dialdehyde).

Reaction equation 3

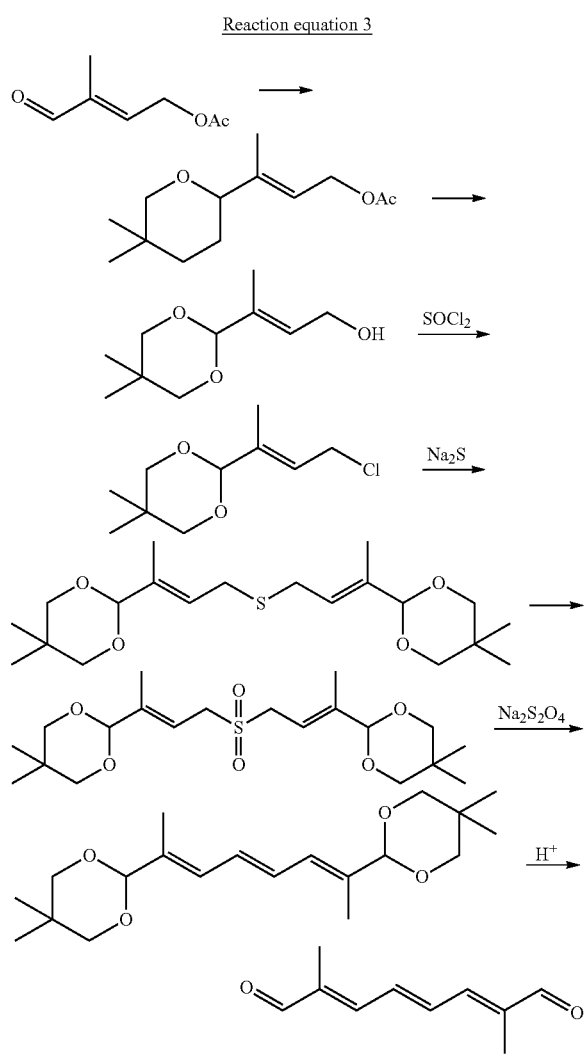

Route 4: sodium benzene sulfinate salt as a bridging agent reacts with two molecular of 2-(3-chloro-1-methyl-1-propenyl)-5,5-dimethyl-1,3-dioxane to produce sulphone compound, and then eliminate phenylsulfonyl through a strong base to obtain C-10 dialdehyde. In fact, the raw material of chloride is used as the same as that of Route 3, and can also be obtained from 4-acetoxy-2-methyl-2-butene-1-aldehyde as a raw material for synthesis of vitamin A, via three steps reaction of acetal protection, basic hydrolysis, and halogenation. The yield of this reaction route is lower, and the total yield is only 15%. The particular reaction scheme is shown as Reaction Equation 4 (synthetic route 4 of C-10 dialdehyde).

Reaction equation 4

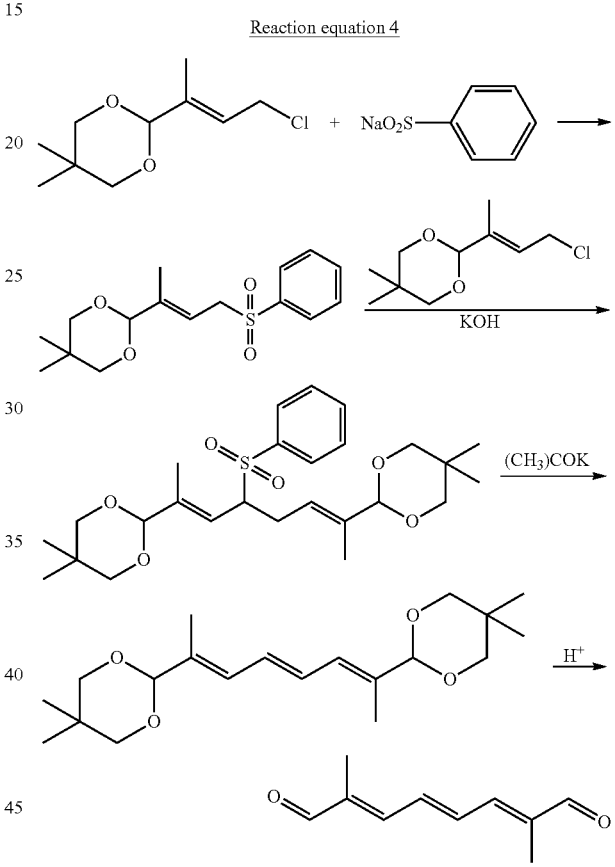

Route 5: propionaldehyde is condensed with methyl formate, and then esterified to prepare 2-methyl-3-alkoxy-2-propenal, the following several reaction steps are basically the same as that of route 2,2-methyl-3-alkoxy-2-propenal is added with acetylene di-Grignard reagent, and deoxidizing triple bond to a double bond, and then form a conjugated double bond through dehydration to obtain C-10 dialdehyde. The particular reaction scheme is shown as Reaction Equation 5 (synthetic route 5 of C-10 dialdehyde).

Reaction equation 5

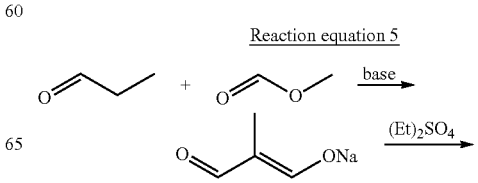

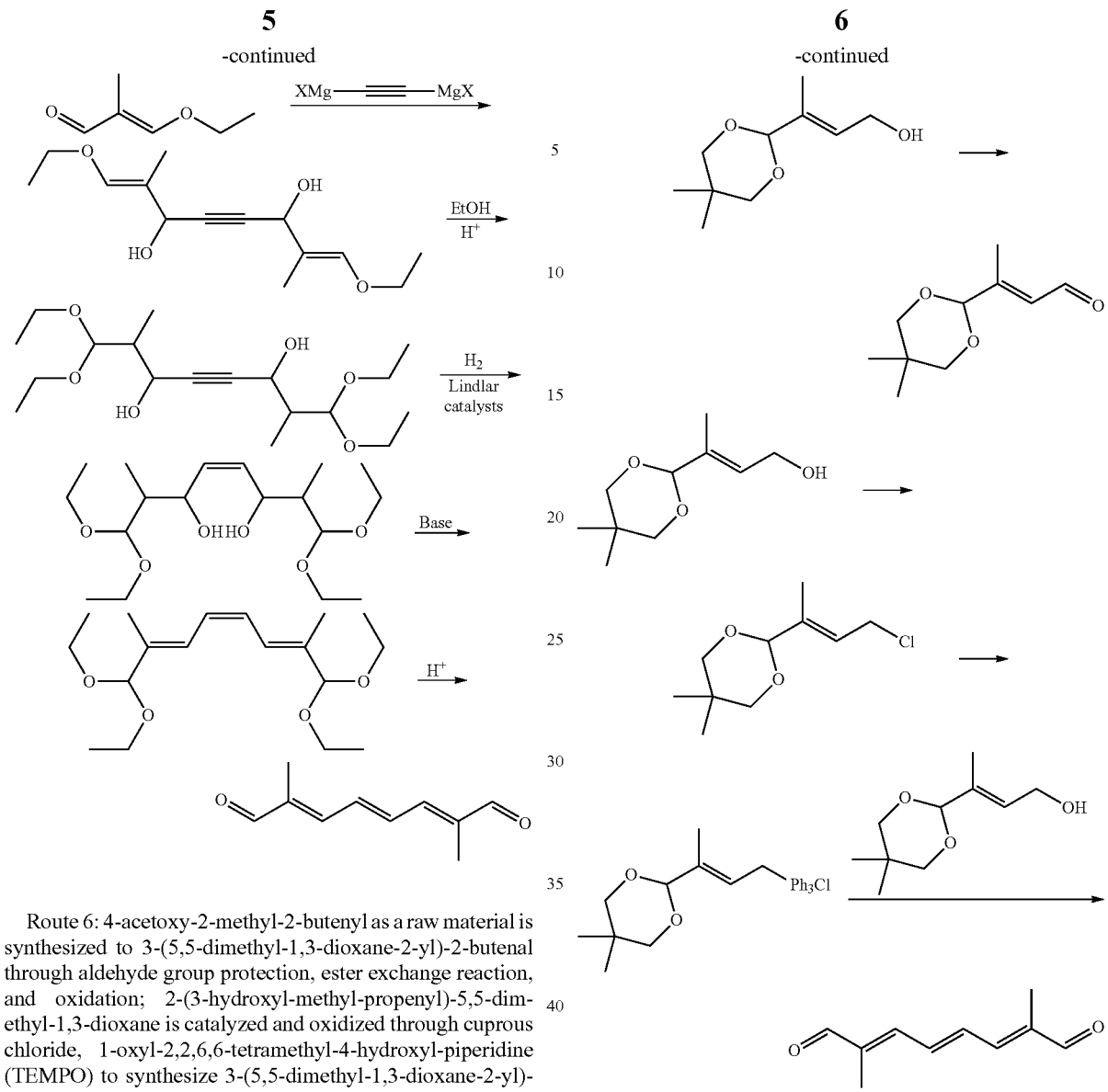

Route 6: 4-acetoxy-2-methyl-2-butenyl as a raw material is synthesized to 3-(5,5-dimethyl-1,3-dioxane-2-yl)-2-butenal through aldehyde group protection, ester exchange reaction, and oxidation; 2-(3-hydroxyl-methyl-propenyl)-5,5-dimethyl-1,3-dioxane is catalyzed and oxidized through cuprous chloride, 1-oxyl-2,2,6,6-tetramethyl-4-hydroxyl-piperidine (TEMPO) to synthesize 3-(5,5-dimethyl-1,3-dioxane-2-yl)-2-butenal; 2-(3-hydroxyl-1-methyl-1-propenyl)-5,5-dimethyl-1,3-dioxane is chlorinated to synthesize 2-(3-chloro-1-methyl-1-propenyl)-5,5-dimethyl-1,3-dioxane; C-10 triene dialdehyde is obtained through the one-pot process of 3-(5,5-dimethyl-1,3-dioxane-2-yl)-2-butenal, 2-(3-chloro-1-methyl-1-propenyl)-5,5-dimethyl-1,3-dioxane and triethyl phosphite. The particular reaction scheme is shown as Reaction Equation 6 (synthetic route 6 of C-10 dialdehyde).

Route 7: 1,4-dihalo-2-butene as a raw material is rearranged to produce disphosphonate compound through Abrozov, and then undergo a Wittig-Horner reaction with acetone dimethyl acetal through deprotection to produce C10 dialdehyde. It was reported that the total yield is 39%[113,121], and the deficiency is that 1,4-dichloro-2-butene or 1,4-dibromo-2-butene as a raw material cannot have a large-scale localization. The particular reaction scheme is shown as Reaction Equation 7 (synthetic route 7 of C10 dialdehyde).

Reaction equation 6

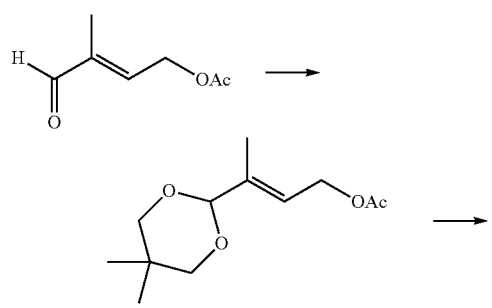

Reaction equation 7

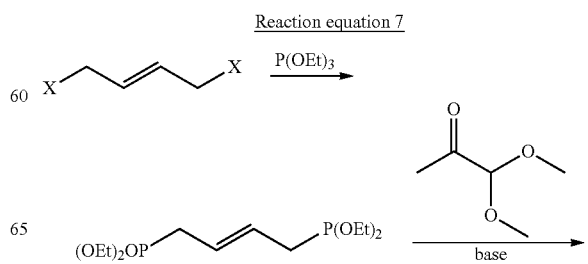

-continued

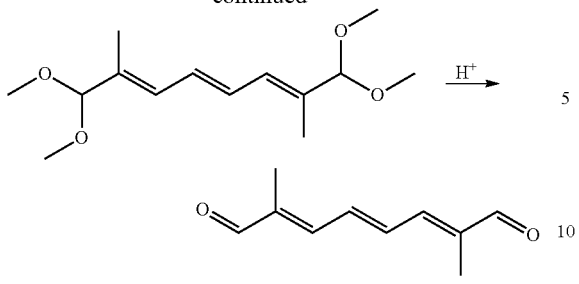

Route 8: NHU Co., Ltd. improves the synthetic method of C10 olefine aldehyde, wherein trans-1,4-dichloro-2-butene as a raw material is synthesized to 2,7-dimethyl-2,4,6-octatriene-1,8-dialdehyde (C10 olefine aldehyde) via Grignard reaction, condensation reaction and acidic hydrolysis reaction. The particular reaction scheme is shown as Reaction Equation 8 (synthetic route 8 of C10 dialdehyde).

Reaction equation 8

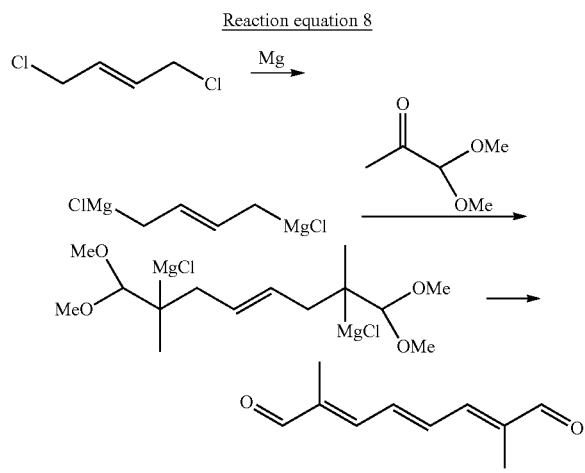

Analyzing the above routes, liquid bromine of route 1 has pollution and large toxicity, the chemical property of allyl methyl ether is active and unstable and easy to produce peroxide which leads to explosion hazard. Route 2 uses acetylene di-Grignard reagent and triple bond partially hydrogenating, and the total yield is only 21%, and consequently is not suitable for industrial production. Both of Route 3 and 4 use 4-acetoxy-2-methyl-2-butene-1-aldehyde as starting material which leads to higher cost and poor economy. The huge deficiency of Route 3 and Route 4 is the biggest obstacle for the industrialization. In Route 5, methyl ether, propionaldehyde, acetylene and dimethyl sulfate are common chemical materials, but it is much easier for propionaldehyde to occur Adol reaction by itself when undergoing Claisen condensation reaction with methyl ether, because of less product and more by-product coming from self condensation, and consequently it has greater difficulty for the separation of product from raw materials and by-products. TEMPO of Route 6 has high cost, and consequently it is difficult to separate raw materials and product when utilizing DNF as solvent. Both of Route 7 and 8 use 1,4-dichlorobutylene as a raw material and is condensed with acetone dimethyl acetal via witting and Grignard reaction, but it has high cost to produce acetone dimethyl acetal, and the di-Grignard reagent prepared by 1,4-dichlorobutylene is extremely unstable, and consequently is not suitable to broadcast in production.

SUMMARY OF THE INVENTION

The present invention provides a new method of synthesizing C10 dialdehyde after analyzing some deficiencies of the above routes. The particular reaction scheme is shown as Reaction Equation 9 (synthetic route 9 of C10 dialdehyde).

Reaction equation 9

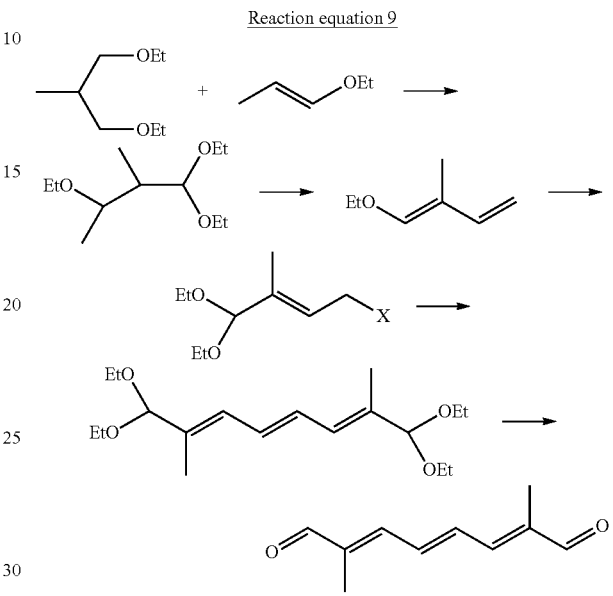

According to the present invention, a method for synthesizing 2,7-dimethyl-2,4,6-octatriene-1,8-dialdehyde comprises the following steps: (1) adding acetaldehyde diethyl acetal (abbreviation: acetal) and ethyl-(1-propenyl)-ether under effects of a catalyst at a temperature of −10° C.~0° C. to produce 1,1,3-triethoxy-2-methyl-butane; wherein the catalyst is ferric chloride or aluminum chloride; acetaldehyde diethyl acetal is prepared by the Chinese Patent No. ZL97115390.6 of Hoffmann-La Roche Ltd; (2) pyrolysis synthesizing 1,1,3-triethoxy-2-methyl-butane under catalytic effects of isoquinoline and p-Toluenesulfonic acid at a temperature of 180-200° C. to produce 1-methoxy-2-methyl-1,3-butadiene; but the catalyst used in the Chinese Patent ZL97115390.6 of Hoffmann-La Roche Ltd. is silicon-aluminum ball, to pyrolysis produce 1-methoxy-2-methyl-1,3-butadiene at high temperature, its conversion rate is only 41%, and its selectivity is 90%; (3) dissolving 1-methoxy-2-methyl-1,3-butadiene in anhydrous ethanol solvent for synthesis with a phase transfer catalyst and a chlorinating agent at a temperature of −5~0° C. to generate 4,4-diethoxy-3-methyl-1-chloro-butene; wherein the phase transfer catalyst is cetyl-trimethyl ammonium bromide, the chlorinating agent is trichloroisocyanuric acid; (4) combining 4,4-diethoxy-3-methyl-1-chloro-butene with a triphenylphosphine salt at a temperature of 60~65° C. to produce a phosphonic salt; and (5) condensing the phosphonic salt under effects of hydrogen peroxide at a temperature of 0~5° C. in conjunction with sodium carbonate solution to generate 1,1,8,8-tetramethyl-2,7-dimethyl-2,4,6-octatriene at pH=8~10; and then hydrolyzing under acidic conditions to synthesize 2,7-dimethyl-2,4,6-octatriene-1,8-dialdehyde.

Preferably, in step (1), the addition reaction undergoes under protections of inert gas. In step (3), potassium acetate is added when 1-methoxy-2-methyl-1,3-butadiene is dissolved in absolute alcohol solvent and the phase transfer catalyst. In step (5), the concentration of hydrogen peroxide is 35 wt. %, the concentration of sodium carbonate solution is 10 wt. %, the acidic condition is 200 ml of 5 wt. % sulphuric acid solution and 100 ml of ethanol.

The present invention has a simple process route, is easy to operate, and has mild conditions, great yield, and great industrial value.

DETAILED DESCRIPTION OF THE PRESENT INVENTION AND PREFERRED EMBODIMENTS THEREOF

Hereafter, the present invention will be described specifically with reference to examples. The examples are given only for illustration of the technical solution of the present invention and should not be construed to limit the present invention.

Example 1

83 g of acetaldehyde diethyl acetal (abbreviation: acetal) and 1 g of ferric chloride are added in 500 ml of four necked bottle under protection of nitrogen, the solution is freezed to −5° C., and kept at −5~0° C., a mixture of 94 g of acetaldehyde diethyl acetal and 86 g (0.945 mol) of ethyl-(1-propenyl)-ether is slowly dropped, and continue to stir it for 10 min after finishing dropping, and the end of reaction is detected by GC. A NaOH solution is added in the reaction to neutralize it to pH=7~8, and to layer, the oil layer is dried by anhydrous sodium sulfate after being washed by water, and heated to 60° C.; most of acetaldehyde diethyl acetal is recycled, to obtain 156.1 g of 1,1,3-triethoxy-2-methyl-butane by vacuum distillation, and its content is 98.5%, and its yield is 81%.

$^1$HNMR (400 MHz, CDCl$_3$) δ(ppm): 0.606 (d, J=6.8 Hz, 3H, (CH)$_2$CHCH*$_3$); 0.798-0.964 (m, 12H, 4CH$_3$); 1.653-1.675 (m, 1H, (CH)$_2$CH*CH$_3$); 3.104-3.306 (m, 6H, 3OCH*$_2$CH$_3$); 3.341-3.436 (m, 1H, OCH*CH$_3$); 4.193 (d, J=5.6 Hz, 1H, OCH*O).

$^{13}$CNMR (100 MHz, CDCl$_3$) δ(ppm): 8.37, 14.95, 15.20, 15.54, 16.89, 40.99, 62.01, 62.31, 63.16, 75.09, 104.11.

DEPT135 (100 MHz, CDCl$_3$) δ(ppm): 8.36, 14.95, 15.20, 15.54, 16.89, 40.98, 62.01(D), 62.31(D), 63.16(D), 75.09, 104.10.

Example 2

236 g of acetaldehyde diethyl acetal (abbreviation: acetal) and 1 g of aluminum chloride are added in 500 ml of four necked bottle under protection of nitrogen, the solution is freezed to −10° C., and kept at −10° C.~−5° C., a mixture of 118 g of acetaldehyde diethyl acetal and 86 g (0.945 mol) of ethyl-(1-propenyl)-ether is slowly dropped, and continue to stir it for 10 min after finishing dropping, and the end of reaction is detected by GC. A saturated NaHCO$_3$ solution is added in the reaction to neutralize it to pH=7, and to layer, the oil layer is dried by anhydrous sodium sulfate after being washed by water, and heated to 50° C.; most of acetaldehyde diethyl acetal is recycled, to obtain 169.6 g of 1,1,3-triethoxy-2-methyl-butane by vacuum distillation, and its content is 97.2%, and its yield is 88%.

Example 3

12.7 g of isoquinoline and 0.69 g of p-toluenesulfonic acid are added in 500 ml three necked bottle, and is stirred by magnetic force, and heated to 220-240° C. of the outer temperature and 180-200° C. of the inner temperature at this moment. 139.5 g (0.684 mol) of 1,1,3-triethoxy-2-methyl-butane is dropped, and the product is distilled out when dropping. The dropping is finished for 6.5 hr, and 125 g of colorless liquid is collected. (the content of ethanol is detected to 34% by GC, and the content of product is 63%), 1-methoxy-2-methyl-1,3-butadiene is distilled under a normal atmosphere, and most of ethanol is distilled out to obtain a bottom material containing 10% of ethanol and 85% of butadiene, and then obtain 74.5 g of product, its content is 97.2%, after rectification under vacuum and at an oil temperature of 100° C.

$^1$HNMR (400 MHz, CDCl$_3$) δ(ppm): 1.268 (t, J=7.2 Hz, 3H, OCH$_2$CH*$_3$); 1.746 (s, 3H, CH$_2$=CCH*$_3$); 3.787-3.861 (m, 2H, OCH*$_2$CH$_3$); 4.797-4.823, 4.942-4.985 (m, 2H, C=CH$_2$); 6.193 (s, 1H, OCH*=CH); 6.265 (dd, J$_1$=10.4 Hz, J$_2$=17.2 Hz, 1H, OCH*=CH).

$^{13}$CNMR (100 MHz, CDCl$_3$) δ(ppm): 8.72, 15.19, 67.95, 107.57, 114.47, 136.81, 147.77.

DEPT135 (100 MHz, CDCl$_3$) δ(ppm): 8.72, 15.19, 67.95 (D), 107.57(D), 136.81, 147.77.

Example 4

On the basis of Example 3, the flask is heated to 220-240° C., and the inner temperature reaches to 180-200° C. at this moment, and 139.5 g (0.684 mol) of 1,1,3-triethoxy-2-methyl-butane is dropped, and the product is distilled out while dropping. The dropping is finished for 5 hr to collect 130 g of colorless liquid. (It is detected by GC that its content of ethanol is 35%, and the content of product is 62%), 1-methoxy-2-methyl-1,3-butadiene is distilled under a normal atmosphere, and most of ethanol is distilled out to obtain a bottom material containing 10% of ethanol and 85% of butadiene, and then obtain 75 g of product, its content is 97.9%, after rectification under vacuum and at an oil temperature of 100° C.

Example 5

46.8 g (0.418 mol) of 1-methoxy-2-methyl-1,3-butadiene, 500 ml of absolute alcohol, 2.0 g of hexadecyl trimethyl ammonium bromide, 20 g of potassium acetate, and 200 ml of toluene are added in 1000 ml of a reaction flask to a solution, and is freezed, 90 g (0.387 mol) of trichloroisocyanuric acid solid is slowly added when an inner temperature is reduced to −5~0° C., the solution becomes milky after the solid is dissolved and then stop the reaction after stirring for 30 min at room temperature. A saturated NaHCO$_3$ is added to neutralize, and is extracted for three times by n-pentane, the oil layer is washed by water for two times, and dried by anhydrous sodium sulfate and filtrated, to obtain 60 g of 4,4-diethoxy-3-methyl-1-chlorobutylene by rectification collection after removing n-pentane. The yield is 74.6%, and the content is 95.6%. (the product in this step is very unstable and needed to be used into the next step soon, and then no further detection is carried out).

Example 6

60 g (0.311 mol) of 4,4-diethoxy-3-methyl-1-chlorobutylene, 100 g (0.382 mol) of triphenylphosphine, 250 ml of methanol are mixed to a mixture and reacted for 2 hr by heat preservation at the temperature of 60~65° C., 100 ml of deionized water is added in the mixture and is extracted and separated for 3-5 times by 500 ml of n-hexane. The n-hexane layer can be applied for reutilization, and the extracted and unreacted triphenylphosphine can be applied for reutilization after crystallization, and extracted by 1000 ml of dichloromethane after recycling methanol of a methanol solution containing phosphonium salt, to obtain 140 g (0.308 mol) of phosphonium salt after removing solvent, and the yield is 99%. The content analyzed by HPLC is 95%.

$^1$HNMR (400 MHz, CDCl$_3$) δ(ppm): 1.162 (t, J=7.2 Hz, 6H, 2OCH$_2$CH*$_3$); 1.396 (s, 3H, CH$_2$=CCH*$_3$); 3.613-3.666 (m, 4H, 2OCH*$_2$CH$_3$); 5.195 (dd, J$_1$=8.0 Hz, J$_2$=16.8 Hz, 2H, CH$_2$P); 6.520-6.538 (m, 1H, CH*C=CH); 7.521-7.572 (m, 1H, CHC=CH*); 7.637-7.696, 73767-7.808, 7.851-7.904 (m, 15H, Ph).

$^{13}$CNMR (100 MHz, CDCl$_3$) δ(ppm): 10.04, 10.06; 18.37; 25.57, 26.07; 58.07; 117.86, 118.91; 130.46, 130.48; 130.57, 130.61; 133.49, 133.53; 135.45, 135.48; 146.01, 146.13.

DEPT135 (100 MHz, CDCl$_3$) δ(ppm): 10.04, 10.06; 18.37; 25.56, 26.06; 58.07; 130.46, 130.48; 130.57, 130.61; 133.49, 133.53; 135.45, 135.48.

Example 7

200 ml of water is added into 40 g (0.088 mol) of phosphonium salt dissolved in 200 ml of dichloromethane to form a solution, and cooled to 0° C. and kept at 0~5° C. 10 g (0.103 mol) of 35% hydrogen peroxide is dropped into the solution for 1 hr, and maintain pH=8~10 with 10% of sodium carbonate solution during dropping, and then continue to stir it at a room temperature for 1 hr, and layer and a red organic layer is washed by 200 ml of water and 100 ml of 10% sulphurous acid, and then layer. 200 ml of 5% sulphuric acid solution and 100 ml of ethanol are added after completely recycling dichloromethane and then stirred at 40° C. for 5 hr, and filtrated, and washed by water, 200 ml of 95% ethanol is added, and then heated and refluxed for 0.5 hr. The solution is cooled to 0° C. and filtrated to produce 11.5 g of a faint yellow needle-shaped crystal after drying under vacuum, the yield of the objective product is 80%.

$^1$HNMR (400 MHz, CDCl$_3$) δ(ppm): 1.920 (s, 6H, 2CH$_3$); 6.730~7.551 (m, 4H, 2CH=CH); 9.542 (dd, J$_1$=8.8 Hz, J$_2$=16.8 Hz, 2H, 2CHO).

$^{13}$CNMR (100 MHz, CDCl$_3$) δ(ppm): 9.7; 130.4; 140.9; 146.2; 194.7.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the invention is intended to cover all alternative constructions and equivalents falling within the spirit and scope of the invention as defined only by the appended claims and equivalents thereto.

The invention claimed is:

1. A method for synthesizing 2,7-dimethyl-2,4,6-octatriene-1,8-dialdehyde, comprising the following steps:
    (1) adding acetaldehyde diethyl acetal and ethyl-(1-propenyl)-ether under effects of a catalyst at a temperature of −10° C.~0° C. to produce 1,1,3-triethoxy-2-methyl-butane; wherein the catalyst is ferric chloride or aluminum chloride;
    (2) pyrolysis synthesizing 1,1,3-triethoxy-2-methyl-butane under catalytic effects of isoquinoline and p-Toluenesulfonic acid at a temperature of 180-200° C. to produce 1-ethoxy-2-methyl-1,3-butadiene;
    (3) dissolving 1-ethoxy-2-methyl-1,3-butadiene in anhydrous ethanol solvent for synthesis with a phase transfer catalyst and a chlorinating agent at a temperature of −5~0° C. to generate 4,4-diethoxy-3-methyl-1-chloro-butene; wherein the phase transfer catalyst is cetyl-trimethyl ammonium bromide, the chlorinating agent is trichloroisocyanuric acid;
    (4) combining 4,4-diethoxy-3-methyl-1-chloro-butene with triphenylphosphine at a temperature of 60~65° C. to produce a phosphonic salt; and
    (5) condensing the phosphonic salt under effects of hydrogen peroxide at a temperature of 0~5° C. in conjunction with sodium carbonate solution to generate 1,1,8,8-tetraethoxy-2,7-dimethyl-2,4,6-octatriene at pH=8~10; and
    then hydrolyzing under acidic conditions to synthesize 2,7-dimethyl-2,4,6-octatriene-1,8-dialdehyde.

2. The method according to claim 1, wherein in step (1), the addition reaction undergoes under protections of inert gas.

3. The method according to claim 1, wherein, in step (3), potassium acetate is added when 1-ethoxy-2-methyl-1,3-butadiene is dissolved in the anhydrous ethanol solvent and the phase transfer catalyst.

4. The method according to claim 1, wherein in step (5), the concentration of hydrogen peroxide is 35 wt. %, the concentration of sodium carbonate solution is 10 wt. %, the acidic condition is 200 ml of 5 wt. % sulphuric acid solution and 100 ml of ethanol.

* * * * *